Nov. 17, 1942. E. N. FRAZEE Plant Pat. 555
FREESIA PLANT
Filed June 18, 1942
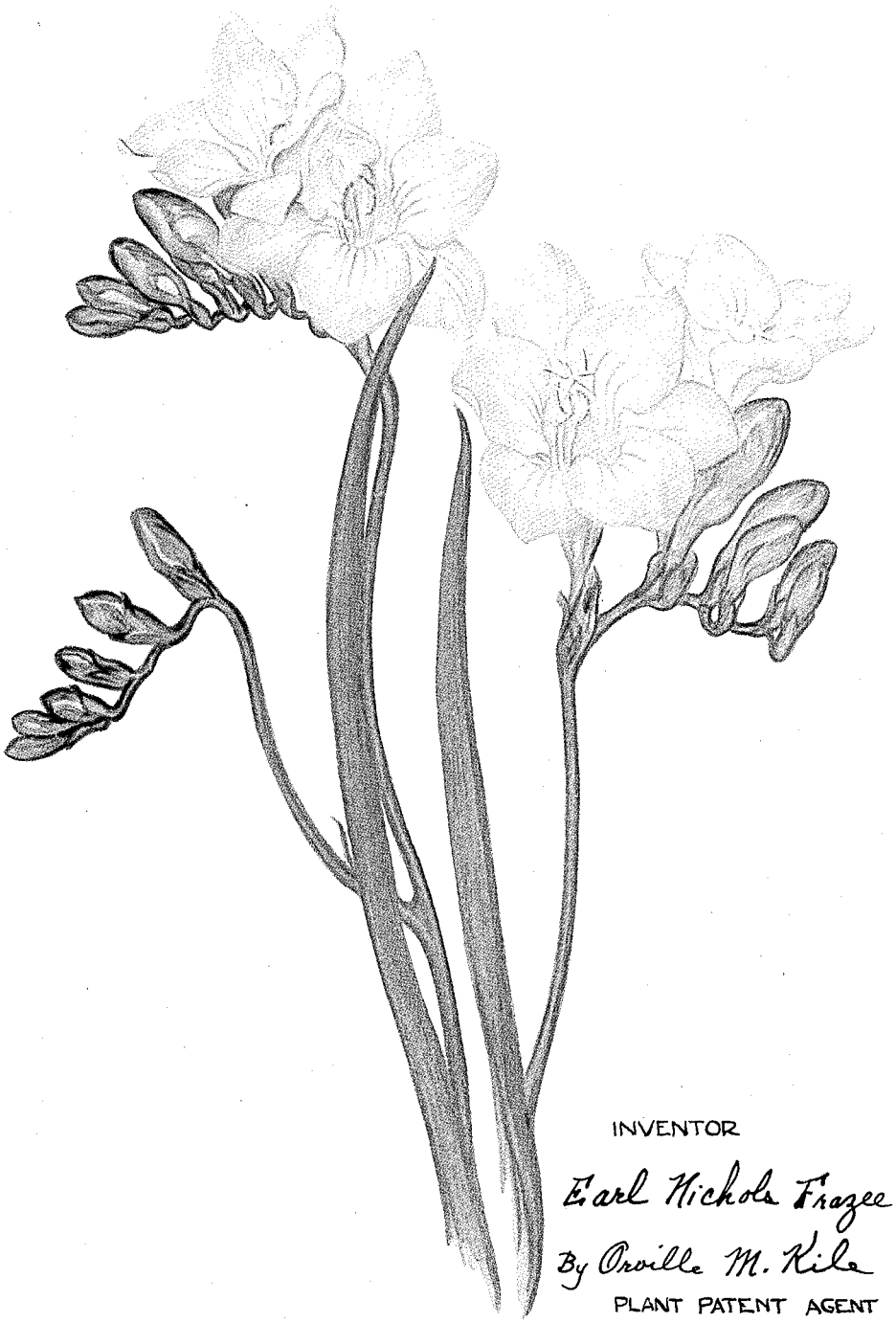
INVENTOR
Earl Nichols Frazee
By Orville M. Kile
PLANT PATENT AGENT Patented Nov. 17, 1942

Plant Pat. 555

UNITED STATES PATENT OFFICE

555

FREESIA PLANT

Earl Nichols Frazee, Oceanside, Calif.

Application June 18, 1942, Serial No. 447,563

1 Claim. (Cl. 47—60)

My new invention relates to improvements in freesia varieties which are used both in the open field and for greenhouse forcing. The principal object of my invention is to produce a freesia variety which is sturdy, vigorous, tall and upright, with early blooming season in which are produced many very large, fragrant blossoms of good substance and novel color.

My new variety resulted from crosses carried on by me at Oceanside, California. I have hybridized freesias for a good many years, selecting and planting seeds from the most desirable-appearing plants and, when they have bloomed, re-selecting those which I wish to keep. However, I have kept no records of these crosses and therefore cannot say just what varieties are the parents of this new variety.

The outstanding features of my new variety are the large size and distinctive color of its flower. Also outstanding is its very early blooming season. When grown in the field in southern California the variety begins to bloom between February 15th and March 1st, depending upon the season. When forced in the greenhouse, the new variety starts blooming the middle of January and continues to bloom to around February 1st. These dates are about two weeks earlier than the blooming dates of most other freesia varieties when grown under similar conditions. We have about a hundred standard varieties of freesias and the new variety blooms earlier than all the rest when grown under similar conditions. This list includes the somewhat similar pink varieties Apothose, Marc Peters and Pinky. Compared with the well-known commercial varieties Purity Superflora and Golden Daffodil, the new variety will bloom ten days earlier under similar conditions.

The original illustration making up a part of this application shows two spikes or branches of the blossoms and a portion of the stems and leaves of the variety, in approximately their true colors.

Following is a detailed description of the flower and plant of the new variety. Color plate references indicate Ridgway's Color Standards and Nomenclature. Where no plate reference is given, the ordinary dictionary term is intended.

*The plant*

Growth habits: A very strong, vigorous and upright grower. Attains a height of 24 inches when grown in greenhouses and of approximately 10 inches when grown outdoors in southern California. Prolific producer of large corms.

Blooming habits: The blooming season is very early, ordinarily between January 15th and February 1st when forced in the greenhouse. Usually there are lateral flower branches which bloom subsequent to the main branches. Produces many fine blossoms.

Stems: Long; upright; strong; bearing flowers in erect position well above the foliage. Their color is a dark rich green, approximately Forest Green (Pl. XVII).

Foliage: Narrow; abundant; very dark, approximately Yew Green (Pl. XXXI); gradually tapering to sharp point; shorter than flower stems.

Bracts: Extra large and substantial; very heavily bronzed; clinging rather than spreading.

*The flower*

Arrangement: Flowers are borne in an upright position along a jointed rachis which extends abruptly from the stem, ordinarily almost at right angles but sometimes drooping at a considerably greater degree. Flowers and buds are close together on the rachis which is heavily bronzed. Six or seven buds and flowers make up the usual flower branch or spike, with two or three of the flowers open at the same time; the lateral flower branches ordinarily having fewer blossoms.

Form: The perianth of the flower is funnel-shaped with little constriction of the throat which is long and tapering. Petals spread to lily-like form or wider.

Size: Approximately 2 inches long and 1½ inches across when outspread, if the plants are greenhouse grown.

Color: The general color effect expressed in common terms is bright orange-pink with throat of yellow shading to cream. Compared with the color chart, the larger portion of the petal is a mixture of Light Jasper Red (Pl. XIII) and Rose Color (Pl. XII). The lower portion of the petal is Light Cadmium Yellow (Pl. IV) with stripings of Eugenia Red (Pl. XIII), the yellow diminishing into cream color as it merges with the pink shades. The throat is translucent, allowing the yellow to show through to the outside of the perianth. The larger buds have a distinctive purplish coloring at their top which merges into yellow on the lower portion.

Petals: Usually six; firm-textured; somewhat pointed; overlapping.

Stamens: White, with long mauve anther.

Pistil: Compound, with three branches which in turn are two-branched. Longer than stamens and extending above them.

Having thus disclosed my invention, I claim:

The new and useful freesia variety herein shown and described, characterized particularly by its vigorous upright growth, including tall upright and strong flower stems and abundant dark green leaves; its extremely early blooming season; its prolific production of large corms; and its very large flowers of heavy substance, splendid keeping qualities and distinctive coloring as indicated.

EARL NICHOLS FRAZEE.